United States Patent [19]
Martin

[11] Patent Number: 5,480,380
[45] Date of Patent: Jan. 2, 1996

[54] COAXIAL DUAL LUMEN CATHETER

[75] Inventor: Geoffrey S. Martin, Mississauga, Canada

[73] Assignee: Med-Pro Design, Inc., Mississauga, Canada

[21] Appl. No.: 264,285

[22] Filed: Jun. 23, 1994

Related U.S. Application Data

[63] Continuation of Ser. No. 31,982, Mar. 16, 1993, abandoned.

[51] Int. Cl.$^6$ ............................................. A61M 3/00
[52] U.S. Cl. ........................... 604/43; 604/280; 604/283; 604/284
[58] Field of Search ................................. 604/39, 43, 44, 604/283, 284, 264, 280, 281, 282, 27, 29, 30, 35, 45

[56] References Cited

U.S. PATENT DOCUMENTS

| | | | |
|---|---|---|---|
| 4,493,696 | 1/1985 | Uldall | 604/43 |
| 4,682,978 | 7/1987 | Martin | 604/43 |
| 5,188,593 | 2/1993 | Martin | 604/280 |

FOREIGN PATENT DOCUMENTS 1284537  8/1972  United Kingdom ................... 604/283

Primary Examiner—John D. Yasko
Assistant Examiner—Ronald K. Stright, Jr.
Attorney, Agent, or Firm—Rogers & Scott

[57] ABSTRACT

The invention provides a dual lumen catheter comprising outer and inner tube materials. A main portion extends axially and has a selected first cross-section. The main portion includes main portions of the respective outer and inner tube materials which together define an annular intake lumen and a main portion of a return lumen contained inside the intake lumen. A tubular transition portion is made up integrally of both the outer and inner tube materials and has a second cross-section smaller than the first cross-section. The transition portion extends axially from the distal end of the main portion and this can be extended to include a tip portion made up only of outer tube material and which extends axially from the transition portion. The transition portion on its own, or with the tip portion, defines a tip section which is a continuation of said main part of the return lumen to complete the return lumen.

20 Claims, 3 Drawing Sheets

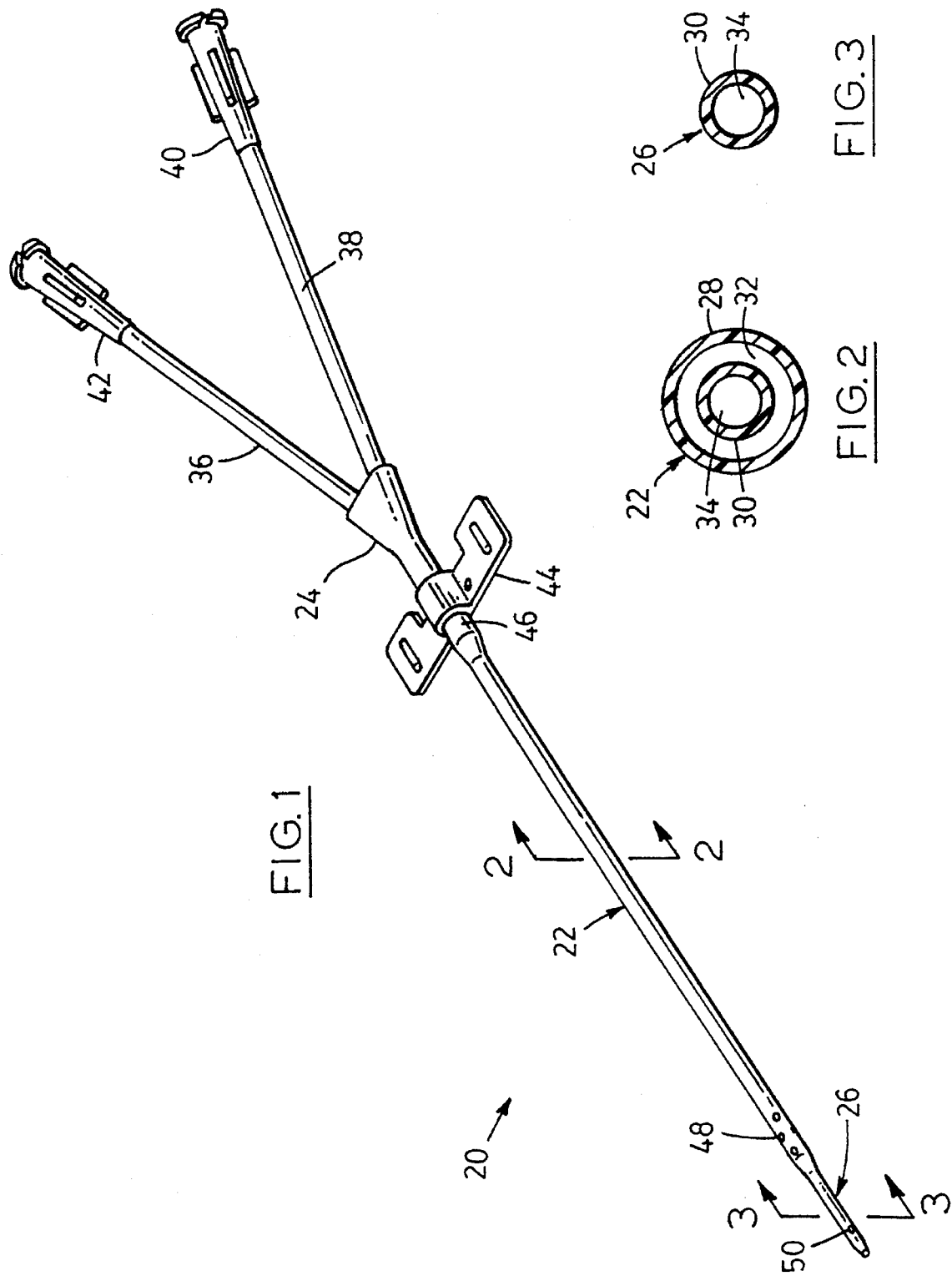

COAXIAL DUAL LUMEN CATHETER

This application is a Continuation of application Ser. No. 08/031,982 filed on Mar. 16, 1993 now abandoned.

This invention relates to dual lumen catheters for use in haemodialysis treatments and more particularly to a dual lumen catheter having intake and return lumens.

BACKGROUND OF THE INVENTION

Haemodialysis treatments have been developed since the early 1960s using a variety of combinations and arrangements of catheters. The earliest treatments were conducted using two needles in the same vein and this subsequently led to pioneer work done by Dr. Shaldon in England who used two flexible catheters which could be left in place for limited periods. Some practitioners proposed the use of a dual flow catheter because this could be entered through a single incision rather than two. From this two basic types were developed. One was a coaxial catheter with the intake lumen surrounding the return lumen, and the other a catheter having side-by-side lumens either in individual tubes connected to one another or in a single extrusion defining two lumens.

Catheters having side-by-side lumens have the disadvantages that because the lumens are side-by-side, the intake openings can be in one side of the catheter only. As a consequence of this, if the catheter were to attach itself to the wall of a vein due to suction applied to the intake lumen, then of course the flow would stop. Medical staff then have to move the catheter by rotating it until blood again flows. This is a very delicate manipulation which is normally performed only by a qualified medical practitioner who must be available at all times in case the flow is discontinued. This disadvantage has resulted in renewed interest in coaxial devices which can be made to have intake openings in any part of the wall of the catheter. As a result, no matter where the catheter may rest against a vein, some of the intake openings remain patent. There is then less likelihood that during use the catheter must be serviced by a trained medical practitioner.

Coaxial catheters are subject to design criteria which can be difficult to meet and which may have contributed to the initial popularity of side-by-side structures. Because the coaxial catheter is inherently less resistant to kinking than side-by-side structures, the tubes used in the structure have had relatively thick walls with the result that the catheter had to also have a larger cross-sectional area than an equivalent side-by-side catheter. One of the reasons for this is that typically the inner tube projected beyond the outer tube to form a distal tip section. Because of this the cross-section of the inner tube has to be chosen to have sufficient rigidity to permit engagement over a Seldinger wire. This consideration set the size of the inner tube.

Another approach is taught by U.S. Pat. No. 4,493,696 to Uldall. The catheter shown in this patent was designed specifically to permit removal of the inner tube between treatments. It was thought at the time of the patent (i.e. about 1980) that such a procedure would be desirable. However, it is now accepted that with modern techniques it is not necessary to remove the inner tube. Also, the inherent disadvantages of accidental separating of the tubes, accurate location of one tube relative to the other, sizing, and the sudden change of section at the end of the inner tube, were all obstacles to the use of this catheter.

The present catheter uses a structure which permits a relatively thin walled inner tube to be used to minimize the overall cross-section of the catheter. Also, the inner tube meets the tip section smoothly to provide a continuous inner lumen at a transition portion where the inner and outer tube materials meet in a permanent bond to minimize the risk of accidental separation and to ensure repeatable manufacturing methods for more constant catheter structures.

SUMMARY OF THE INVENTION

Accordingly, in one of its aspects, the invention provides a dual lumen catheter comprising outer and inner tube materials. A main portion extends axially and has a selected first cross-section. The main portion includes main portions of the respective outer and inner tube materials which together define an annular intake lumen and a main part of a return lumen contained inside the intake lumen. A tubular transition portion is made up exclusively of both the outer and inner tube materials and has a second cross-section smaller than the first cross-section. The transition portion extends axially from the distal end of the main portion and this can be extended to include a tip portion made up only of outer tube material and which extends axially from the transition portion. The transition portion on its own, or with the tip portion, defines a tip section which is a continuation of said main part of the return lumen to complete the return lumen.

BRIEF DESCRIPTION OF THE DRAWINGS

This invention will be better understood with reference to the drawings in which:

FIG. 1 is an isometric view of a preferred embodiment of a catheter according to the invention;

FIG. 2 is a sectional view on line 2—2 and drawn to a larger scale;

FIG. 3 is a sectional view on line 3—3 of FIG. 1 and drawn to the same scale as FIG. 2;

DESCRIPTION OF THE PREFERRED EMBODIMENT

Figure 6:
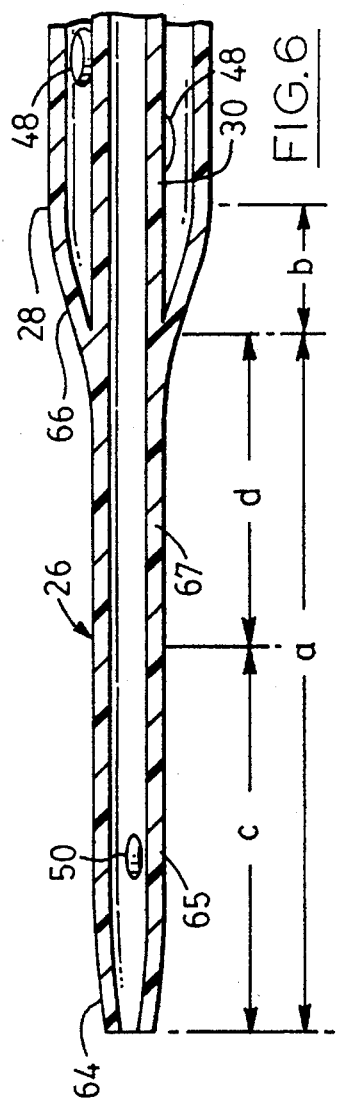
FIG. 6 is a sectional view of a finished distal end of the catheter.

Reference is first made to FIG. 1 which illustrates a catheter designated generally by the numeral 20 and consisting of the main portion 22 extending from a trident shaped connector 24 to a distal tip section 26. As seen in FIG. 2, the main portion 22 is made up of an outer tube material 28 and an inner tube material 30 spaced radially from one another to define an annular intake lumen 32 and a circular return lumen 34. The return lumen 34 continues beyond the main portion 22 and into the tip section 26 as indicated by the section at FIG. 3. However, there is a transition between the main portion 22 and the tip section involving both the outer and inner tube materials 28, 30 as will be described.

At the proximal end, the trident shaped connector 24 has connected to it respective intake and return tubes 36, 38 having the usual luer connectors 40, 42 to make connection to tubing associated with a dialysis machine or the like.

The connector 24 has internal channels connecting the tubes 36, 38 to the respective lumens 32, 34 (FIG. 2) as will be described more fully with reference to FIGS. 7 and 8.

The catheter is completed by the inclusion of a rotatable suture wing 44 mounted on the main section and held in place by a collar 46 locating the wing 44 against the connector 24 for longitudinal positioning of the wing.

As also seen in FIG. 1, the catheter has side openings 48, 50. The openings 48 are spaced circumferentially around the catheter to provide access to the intake lumen 32 and optional side openings 50 are provided adjacent the distal end of the catheter to permit a flow from the return lumen 34.

Figure 4:
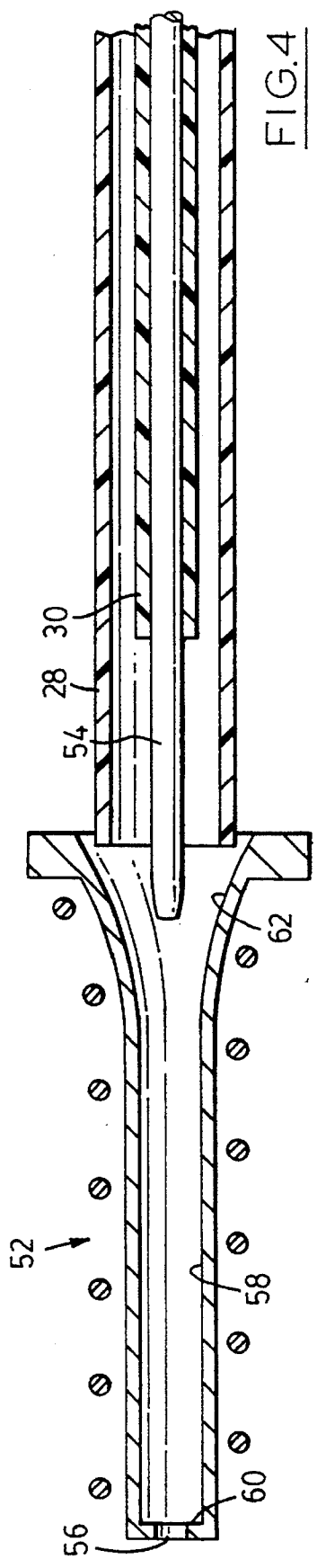
FIG. 4 is a diagrammatic view of a step in the manufacture of a distal end of the catheter.
Figure 5:
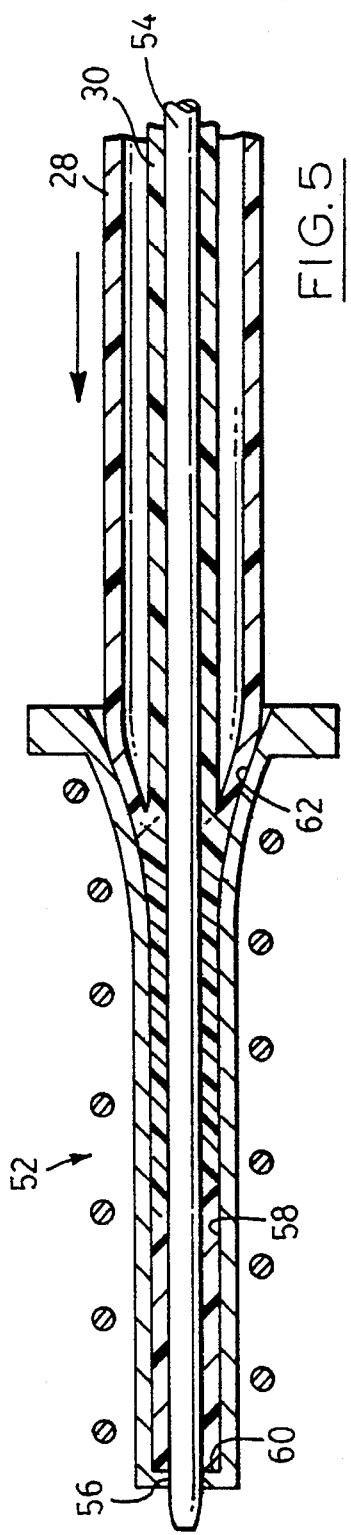
FIG. 5 is a view similar to FIG. 4 and showing a subsequent step in the manufacture of the distal end.

The structure of the tip section 26 will be better understood with reference to the method of manufacture which is illustrated in FIGS. 4 and 5.

Reference is next made to FIG. 4 which is a diagrammatic illustration of the early steps in the manufacture of the tip section. As seen in FIG. 4, outer tube material 28 in the form of an extruded round tube is positioned adjacent a RF heating device 52 and contains inner tube material 30 also in the form of an extruded tube of round cross-section. This latter tube has a thinner wall than the outer tube, but this is not shown in order to simplify the drawings.

The material 30 contains a round stainless steel mandrel 54 which projects beyond the distal extremity of the outer tube material 28 and is shaped for engagement in an opening 56 at the inner end of the device 52. This device has an internal shape matching that of the required tip section and includes a tubular main portion 58 extending outwardly from a back wall 60 containing the opening 56, and ending at flared entrance 62 which blends into the main portion 58 with a curvature to be given to the catheter. It will be seen that the inner tube material 30 has an inner diameter matching the outer diameter of the mandrel 54 and the distal end of the outer tube material 30 terminates inwardly of the distal end of the inner tube material 28 by a distance equal to about one quarter of the length of the cavity in the RF device 52.

Once the parts are arranged as shown in FIG. 4, the RF device 52 is energized to heat the device to a temperature sufficient to cause flow in the thermoplastic materials 28, 30. Once heating has been achieved, the parts shown in FIG. 4 are moved into the device 52 in unison and this movement continues until they take up the position shown in FIG. 5. It will be evident from the arrangement in FIG. 4 that the end of the mandrel 54 is first engaged in the opening 56 and then the distal end of the outer tube material 28 meets the wall 60 and this ensures that the material about the mandrel forms a constant wall thickness. While this is happening, the distal end of the inner tube material 30 will meet the converging outer wall material 28 and because of the heat, the two will blend into one unitary wall over a significant length of the device 52, indicated by a separate and closer form of cross-hatching in FIG. 5. This is better illustrated in FIG. 6.

As seen in FIG. 6, tip section 26 has a length "a" which may include a tapered tip portion 64 formed either during or after the procedure described with reference to FIGS. 4 and 5. The purpose of this is simply to improve the utility of the catheter when used in association with a Seldinger wire which is fed through the centre of the catheter.

As also seen in FIG. 6, the tip section 26 is made up of a tip portion 65 having a length "c" and a transition portion 67 having a length "d" corresponding to the closer cross-hatching mentioned with reference to FIG. 5. Portion 65 is made up of the outer tube material 28 whereas portion 67 is made up of both outer and inner tube materials 28, 30. There is also a tapered portion 66 having a length "b" made up of the outer tube material.

This arrangement of manufacture permits a relatively light thin walled inner tube material 30 to be used within more robust outer tube material 28. The resulting return lumen 34 (FIG. 2) is smooth walled and continuous and is made up of outer tube material 28 at the tip portion 65, both outer and inner tube materials 28, 30 at the transition portion 67, and of a main portion of the inner tube material alone over the main part of the return lumen corresponding to portion 22 (FIG. 1) of the catheter. Similarly, a main portion of the outer tube material defines a main portion 22 of the catheter.

As mentioned, it is desirable that the inner tube material 30 have a relatively thin wall in order to minimize the space lost to flow within the outer tube material 28, and consequently to reduce the area of cross-section of the catheter. Because the outer tube material 28 is sufficiently robust, it can be used advantageously to form the tip portion 65.

It will also be appreciated that because the outer tube material 28 is being reduced in diameter as it is deformed, it will lengthen. Consequently the length of the tip section is a function of the reduction in diameter and wall thickness.

Figures 7, 8:
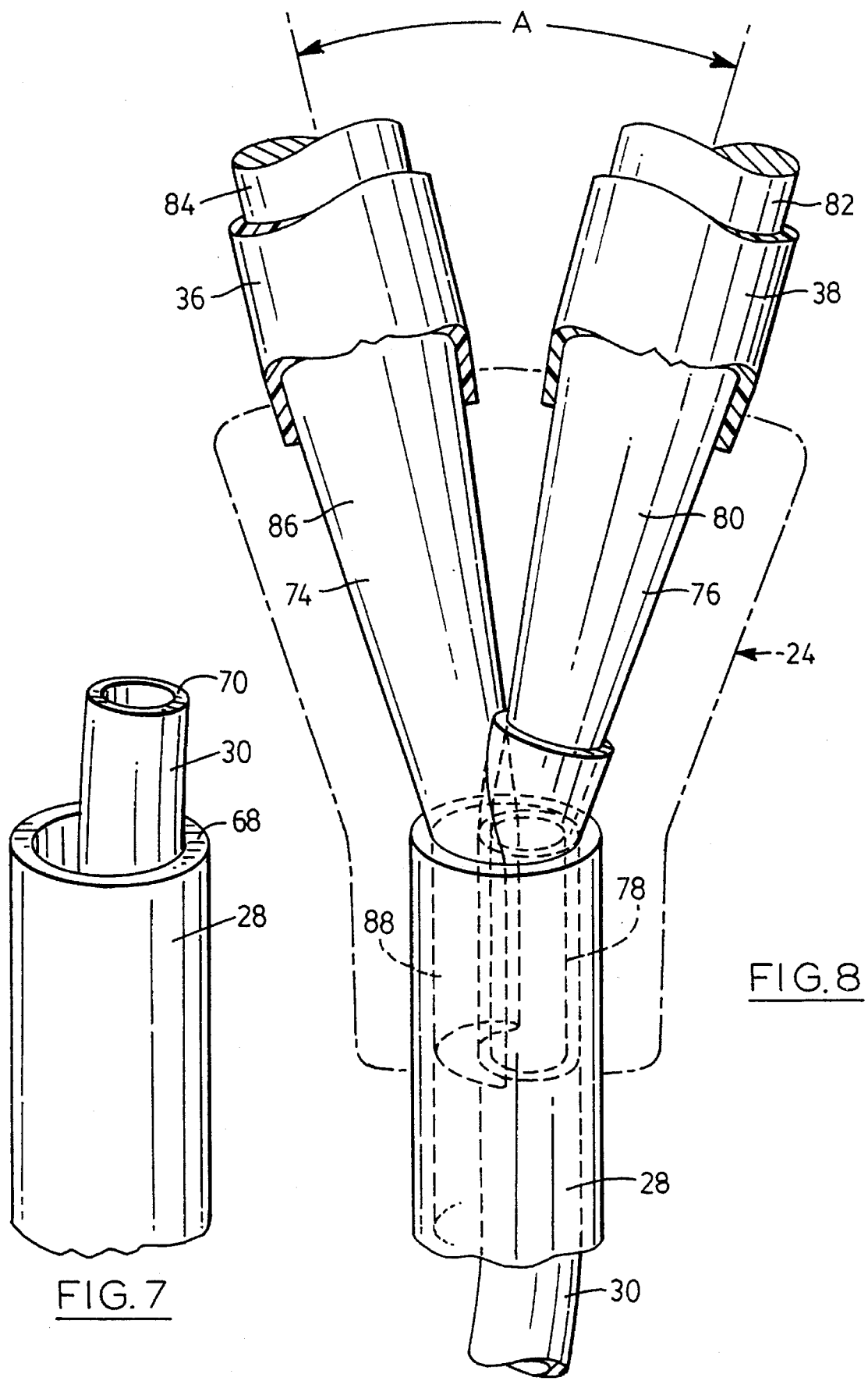
FIG. 7 is an isometric view of a proximal end of the main portion of the catheter during manufacture of the proximal end.
FIG. 8 is a diagrammatic representation of the proximal end prepared ready for moulding a connector at the proximal end of the main body.

Reference is next made to FIGS. 7 and 8 which illustrate a method of making the connector 24 and also show details of the connector. As seen in FIG. 7, proximal ends 68, 70 of the outer and inner tube materials 28, 30 are positioned so that the inner tube material projects outwardly beyond the outer tube material. With this arrangement, a pair of first and second mandrels 74, 76 are engaged as shown in FIG. 8. The mandrel 76 has a leading cylindrical portion 78 blending outwardly into a converging and generally conical portion 80, which in turn blends into a cylindrical end part 82 angled with respect to the portion 80. The cylindrical portion 78 is engaged in the inner tube material 30 and pushed into place so that there is a slight flaring of this material as it engages on the conical portion 80.

Mandrel 74 is then engaged. This mandrel has an outer cylindrical portion 84 which blends into a converging and generally conical portion 86 ending at a projection 88. This projection has a generally U-shaped configuration and is angled with respect to the conical portion 86.

The U-shaped projection 88 on the end of the mandrel 74 is shaped to fit the space provided when the inner tube material 30 is held against the inner surface of the outer tube material 28. (i.e. in the position shown in FIG. 7). As a result there is a generally U-shaped space between the inner and outer tube materials which is filled by the projection 88. The angular offsets of the cylindrical portion 78 of mandrel 76 and the projection 88 of mandrel 74 result in these parts extending axially with respect to the catheter while the cylindrical end part 82 and cylindrical portion 84 of the mandrels diverge at an angle "A" indicated in FIG. 8. These cylindrical parts receive respective intake tubes 36 and 38 which are positioned as shown in FIG. 8. Once the assembly shown in FIG. 8 has been completed, the mould is closed and injection takes place to form the connector 24 shown in chain-dotted outline. This outline of course also represents the cavity of the mould.

The material used for all of the parts is preferably polyurethane, including the moulded connector 24, although other materials can be used provided that the usual requirements of compatibility, etc. are met.

After moulding and cooling, the mandrels 74, 76 are removed and because there is flexibility in the material, and because the mandrels are smooth, the mandrels can be pulled out without causing any damage.

It will be evident that this arrangement of connector provides for a smooth transition from the respective intake and return tubes 36, 38 to the respective intake and return lumens 32, 34 (FIG., 2) in the main body of the catheter.

It is sufficient to note that the angle "A" shown in FIG. 8 can be kept to a small angle in the order of 15 to 20 degrees and is readily maintained below 30 degrees. As a result, the flow into and out of the catheter is essentially axial with reference to the main section 34 at all times. This is desirable in situations where the catheter has to be positioned such that the connecting tubes 36, 38 are as near in line with the catheter as possible.

In a typical catheter to be used for haemodialysis, the inner tube material 28 has an outside diameter of 11.5 French and a wall thickness of 0.45 mm, and the inner tube material has an outside diameter of 6.5 French and a wall thickness of 0.19 mm. The dimensions shown in FIG. 6 are approximately: a=30 mm; b=4 mm; c=17 mm; and d=13 mm. The distance between the ends of the outer and inner tube materials 28, 30 in FIG. 4 is about 6 mm and the travel in the RF device 52 is about 25 mm resulting in about 2–3 mm increase in length.

One possible variation from the preferred embodiment is to arrange for the distal end of the catheter to coincide with the distal end of the transition portion 59 (FIG. 6). However, it is preferred to include the tip portion 57.

It is clear that the preferred embodiment described is exemplary of the coaxial lumen catheters generally and that the details and dimensions given are only. Such other structures are within the scope of the invention as claimed.

I claim:

1. A dual lumen catheter comprising:

outer tube material and inner tube material;

a main portion extending axially between proximal and distal ends and having a selected first cross-sectional area, the main portion of the catheter including respective main portions of the outer tube material and the inner tube material and defining an annular intake lumen between the main portions of the inner and outer tube materials and a main part of a return lumen defined by the inner tube material, the main portion of the outer tube material terminating at the distal end of the main portion of the catheter in a converging tapered portion, and the main portion of the catheter having a plurality of side openings in the outer tube material adjacent the distal end of the main portion of the catheter, the openings being spaced around the main portion of the catheter to provide access into the intake lumen;

a tubular transition portion made of both outer and inner tube materials blended together integrally, and having a second cross-section smaller than said first cross-sectional area, the transition portion extending distally from said tapered portion;

a tip portion made up exclusively of outer tube material and extending distally from the transition portion and being a continuation of the transition portion whereby the tip portion and the transition portion define a tip section which includes a return lumen part which, together with said main part of the return lumen, forms a return lumen having substantially constant cross-section;

a connector attached to the proximal ends of the inner and outer tube materials; and intake and return tubes attached to the connector for continuous fluid communication with the respective intake and return lumens whereby the catheter can be used for procedures requiring dual flow through a single catheter.

2. A catheter as claimed in claim 1 in which the inner tube material has a wall thickness less than the wall thickness of the outer tube material.

3. A catheter as claimed in claim 2 in which the return lumen is round in cross-section and in which the main portion of the outer tube material is round in cross-section.

4. A catheter as claimed in claim 1, in which the tip section defines at least one further side opening to permit flow from the return lumen.

5. A catheter as claimed in claim 1 in which the return lumen is round in cross-section and in which the main portion of the outer tube material is round in cross-section.

6. A coaxial catheter comprising:

a main portion of inner tube material defining a main part of a return lumen extending axially;

a main portion of outer tube material containing the main part of the return lumen and spaced radially from the inner tube material to define an annular intake lumen;

a transition portion integrally attached to respective inner and outer tube materials and forming a smooth continuation axially of said main portion of the return lumen and including portions of said inner and outer tube materials blended into a unitary wall;

a tip portion extending axially from the transition portion and forming a smooth continuation of said transition portion of the return lumen and also having the same cross-section as the return lumen, the tip portion being exclusively of said outer tube material, and defining a distal end of the catheter;

openings in the main part of the outer tube material adjacent the transition portion to provide access into the intake lumen;

a connector attached to the proximal ends of the respective main portions of the inner and outer tube materials; and intake and return tubes attached to the connector for continuous fluid communication with the respective intake and return lumens whereby the catheter can be used for procedures requiring dual flow through a single catheter.

7. A catheter as claimed in claim 6 in which the inner tube material has a wall thickness less than the wall thickness of the outer tube material.

8. A catheter as claimed in claim 7 in which the return lumen is round in cross-section and in which the main portion of the outer tube material is round in cross-section.

9. A catheter as claimed in claim 6 in which the tip portion defines at least one further side opening adjacent said distal end of the catheter to permit flow from the return lumen.

10. A catheter as claimed in claim 6 in which the return lumen is round in cross-section and in which the main portion of the outer tube material is round in cross-section.

11. A coaxial catheter comprising:

a main portion of inner tube material defining a main part of a return lumen extending axially;

a main portion of outer tube material containing the main part of the return lumen and spaced radially from the inner tube material to define an annular intake lumen;

a tip section including a transition portion integrally attached to the distal ends of the respective main portions of the inner and outer tube materials and forming a smooth continuation axially of said main part of the return lumen, the transition portion being made of said inner and outer tube materials;

openings in the main portion of the outer tube material adjacent the transition portion to provide access into the intake lumen;

a connector attached to proximal ends of the main portions of the inner and outer tube materials; and intake and return tubes attached to the connector for continuous fluid communication with the respective intake and return lumens whereby the catheter can be used for procedures requiring dual flow through a single catheter.

12. A catheter as claimed in claim 11 in which the main portion of the inner tube material has a wall thickness less than the wall thickness of the main portion of the outer tube material.

13. A catheter as claimed in claim 12 in which the return lumen is round in cross-section and in which the main portion of the outer tube material is round in cross-section.

14. A catheter as claimed in claim 11 in which the tip portion defines at least one further side opening to permit flow from the return lumen.

15. A catheter as claimed in claim 11 in which the return lumen is round in cross-section and in which the main portion of the outer tube material is round in cross-section.

16. A coaxial catheter comprising:

a main portion having a selected cross-section and extending axially between proximal and distal ends;

a tip section extending axially from said distal end and blending smoothly into said main portion;

the main portion having inner and outer tube materials defining an outer annular intake lumen and a main part of an inner return lumen contained within the intake lumen;

the tip section defining a further part of the return lumen and extending continuously from said main part to combine with said main part to define a continuous smooth return lumen free of irregularities, the tip section including material from both the inner and outer materials blended together;

openings in the outer tube material adjacent the tip section to provide access into the annular intake lumen;

a connector attached to the proximal ends of the inner and outer tube materials; and intake and return tubes attached to the connector for continuous fluid communication with the respective intake and return lumens whereby the catheter can be used for procedures requiring dual flow through a single catheter.

17. A catheter as claimed in claim 16 in which the return lumen is round in cross-section and in which the main portion of the outer tube material is round in cross-section.

18. A catheter as claimed in claim 16 in which the inner tube material has a wall thickness less than the wall thickness of the outer tube material.

19. A catheter as claimed in claim 16 in which the inner tube is located against the outer tube inside the connector.

20. A catheter as claimed in claim 16 in which the tubes leave the connector with an angle of divergence between 15 and 30 degrees.

* * * * *

UNITED STATES PATENT AND TRADEMARK OFFICE
CERTIFICATE OF CORRECTION

PATENT NO. : 5,480,380
DATED : January 2, 1996
INVENTOR(S) : Geoffrey S. Martin

It is certified that error appears in the above-identified patent and that said Letters Patent is hereby corrected as shown below:

Column 4,
Line 10, change "wailed" to -- walled --.

Column 5,
Line 33, after "given are" insert -- exemplary --.

Signed and Sealed this

Nineteenth Day of March, 2002

Attest:

Attesting Officer

JAMES E. ROGAN
Director of the United States Patent and Trademark Office